United States Patent [19]

Robinson

[11] 4,068,162

[45] Jan. 10, 1978

[54] RINSE TANK CONTROL SYSTEM

[75] Inventor: Myron L. Robinson, Solana Beach, Calif.

[73] Assignee: Simekus, Inc., Vista, Calif.

[21] Appl. No.: 710,627

[22] Filed: Aug. 2, 1976

[51] Int. Cl.² ............................................ G01N 27/42
[52] U.S. Cl. .................................... 324/30 B; 324/29; 324/72.5
[58] Field of Search ............... 204/304; 324/29, 30 R, 324/30 B, 58.5 C, 65 CR, 65 P, 72.5

[56] References Cited
U.S. PATENT DOCUMENTS

| | | | |
|---|---|---|---|
| 3,262,051 | 7/1966 | Payne, Jr. | 324/29 |
| 3,365,376 | 1/1968 | Weyland | 324/29 |

FOREIGN PATENT DOCUMENTS

| | | | |
|---|---|---|---|
| 982,290 | 2/1965 | United Kingdom | 324/30 B |

Primary Examiner—M. Tokar

Attorney, Agent, or Firm—Harris, Kern, Wallen & Tinsley

[57] ABSTRACT

A control system for a water rinse tank or the like which continuously monitors the rinse water quality by means of electrical conductivity and adds clean water when the water-contamination conductivity of the rinse water builds up through use to a predetermined value. A conductivity cell which is transparent and may be disassembled, and adjustable for operation over a wide range of conductivity settings. A power circuit with triac for switching power to a valve solenoid. A silicon controlled rectifier (SCR) and its associated circuitry located at the conductivity cell for controlling the triac, with the SCR operation directly controlled by the conductivity cell. A zener diode-transistor voltage regulating circuit for consistently maintaining substantially the same spiked waveform across the conductivity cell both for water off and water on conditions.

20 Claims, 9 Drawing Figures

U.S. Patent  Jan. 10, 1978  Sheet 1 of 2  4,068,162
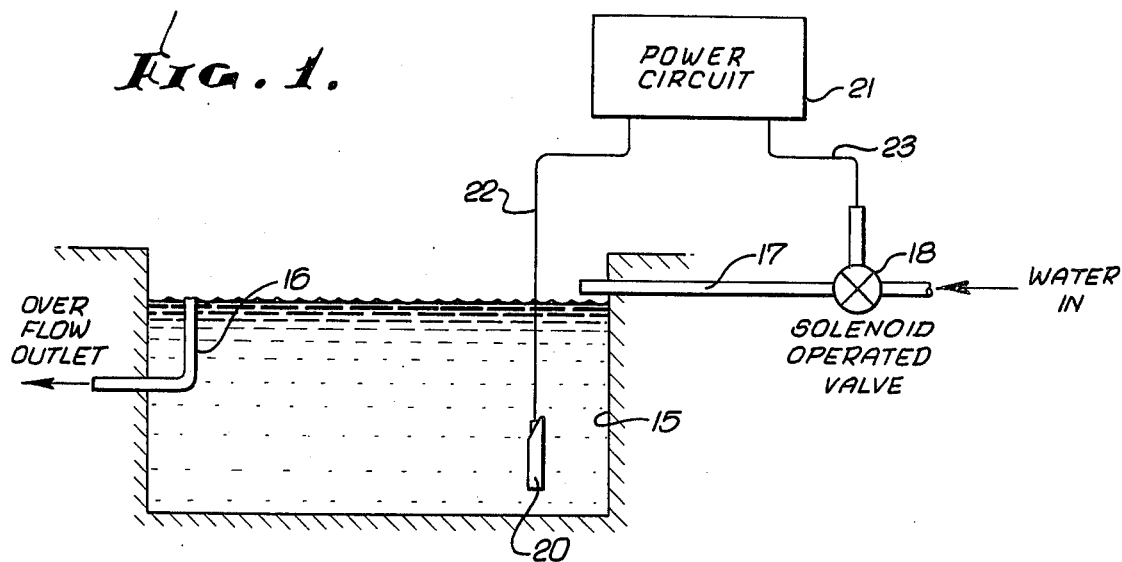
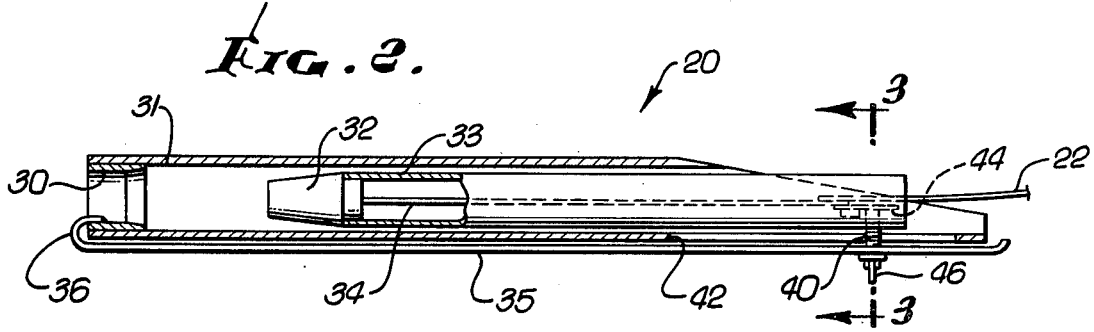
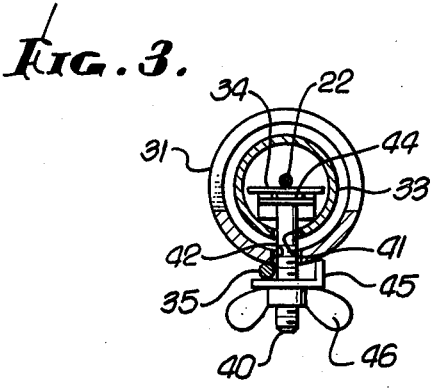
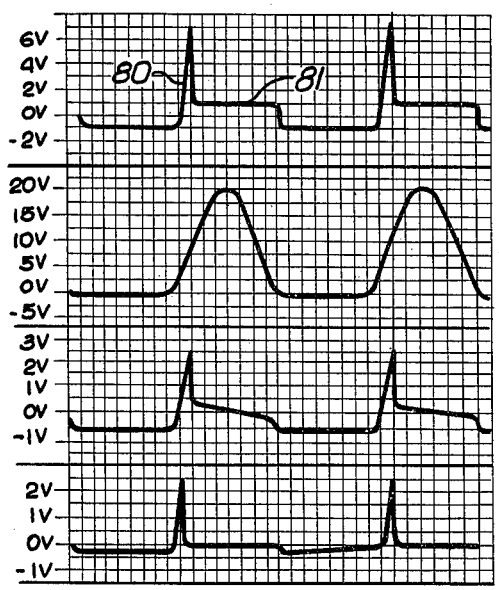

RINSE TANK CONTROL SYSTEM

BACKGROUND OF THE INVENTION

This invention relates to the control of water quality in a rinse tank, such as the tanks which are widely used in electroplating plants. In the simplest form of rinse tank, clean water is continuously introduced at one side of the tank, with an overflow line at the opposite side of the tank. However this procedure results in considerable waste of water since water flow is not related to water quality. Control systems are in use today which measure the electrical conductivity of the water and add clean water only when the conductivity increases above some preset figure, with the conductivity being related to the contaminants in the rinse water.

These prior art systems utilize a conductivity cell with fixed configuration positioned in the water and an electronic circuit separate from and connected to the cell for providing the control if the inlet water valve. The conductivity set point for turning on the water supply is adjusted in the electronics. Because of the severe chemical and electrical conditions in the environment of most industrial electroplating plants, the desired stability and precision of operation has been achieved only by resorting to expensive and complex electronics and cell materials.

Accordingly, it is an object of the present invention to provide a new and improved control system for a water rinse tank of the like. A particular object is to provide a new and improved conductivity cell for use with such a control system, with a cell configuration that is adjustable to provide operation over a wide range of set points. A further object is to provide such a system in which the electronics can be incorporated in the cell structure for positioning within the tank providing improved environmental stability without complex circuitry and requiring only two nonpolarized, unshielded wires as a cable from the cell. Another object of the invention is to provide a new and improved control circuit for use with the conductivity cell with the circuit providing substantially the same ideal waveform at the cell irrespective of line voltage and frequency irregularities thereby insuring that the cell always operates under the same optimum conditions regardless of contamination of the cell surfaces.

SUMMARY OF THE INVENTION

The present invention includes a control system for use in a rinse tank having a water inlet line and a valve for controlling flow in the inlet line and including a conductivity cell and control circuit for positioning in the tank and a power circuit for operating the valve as a function of conductivity.

The control circuit including a first rectifier connected across ac supply terminals with one polarity and a second controlled rectifier connected across the terminals with the opposite polarity. The second rectifier preferably is a silicon controlled rectifier (SCR). A voltage divider is also connected across the terminals with a point of the divider connected to the control electrode of the SCR for firing the SCR. The conductivity cell is connected to the divider circuit in shunt relation with the control electrode and another circuit is connected to the divider circuit in shunt relation with the cell providing for reducing the voltage across the cell when the voltage at the ac terminals exceeds a predetermined value during periods of non-conduction of the SCR. This control circuitry is located at the conductivity cell to provide automatic temperature compensation by the temperature sensitivity of the SCR gate.

The control system maintains precision control of rinse water quality irrespective of severe environmental conditions. Also the system requires few parts, none of which are critical, and can initially be manufactured easily and economically in low volume from readily available materials yet later can be manufactured in greater volume using molded and plated parts. In addition, the cell provides stability to the chemical and electrical environment; can be seen through, and can be disassembled for convenient field inspection and service.

The conductivity cell includes two separate and spaced electrodes and a configuration for moving one of the electrodes relative to the other for adjusting the conductivity set point. The cell is transparent and may be disassembled for inspection and service.

BRIEF DESCRIPTION OF THE DRAWINGS

FIG. 1 is a diagramatic view of a water rinse tank with the control system of the present invention installed therein;

FIG. 2 is a sectional view through the conductivity control unit of the system of FIG. 1 incorporating the conductivity cell and associated electronics;

FIG. 3 is an enlarged sectional view taken along the line 3—3 of FIG. 2;

FIGS. 6 and 7 are waveforms of the voltage at the terminals 10, 11 of FIGS. 4 and 5 for the solenoid off and solenoid on conditions, respectively; and FIGS. 8 and 9 are waveforms for the voltage across the conductivity cell for the solenoid off and solenoid on conditions, respectively.

DESCRIPTION OF THE PREFERRED EMBODIMENT

Figure 4:
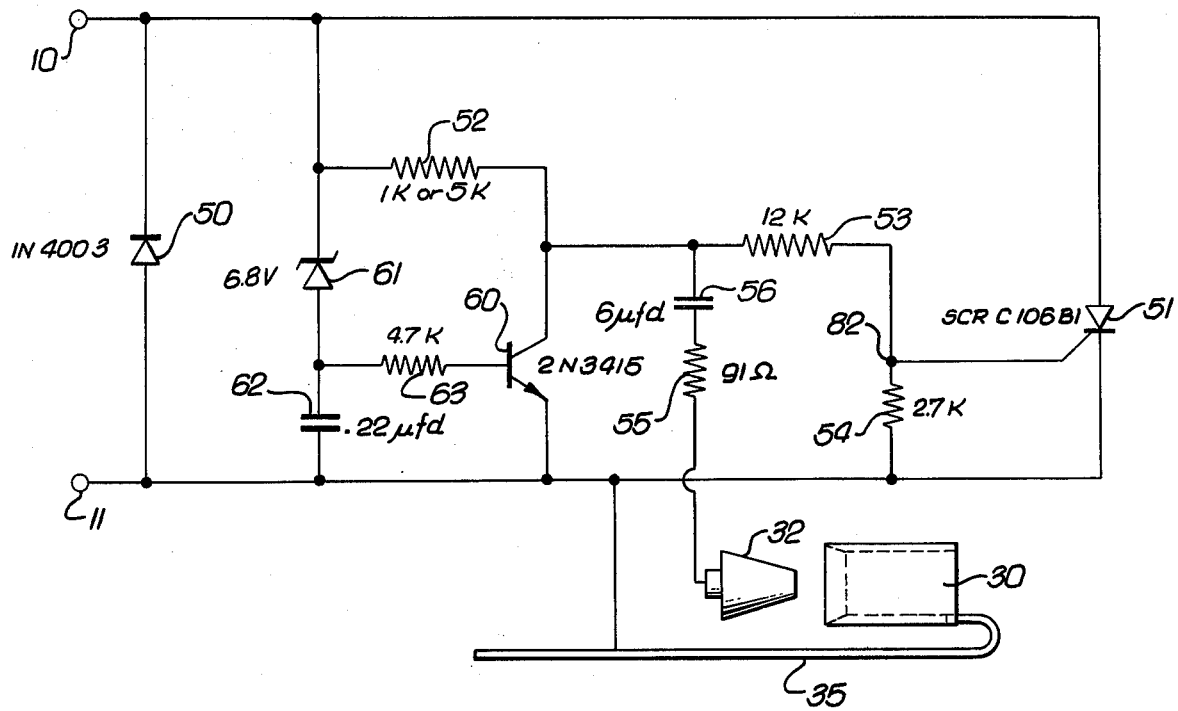
FIG. 4 is an electrical schematic of the control circuit and the conductivity cell.

FIG. 1 illustrates a rinse tank 15 with an overflow outlet pipe 16 and an inlet 17. Flow of water through the inlet pipe 17 is controlled by a solenoid operated valve 18. A conductivity control unit 20 is positioned in the water in the tank 15. A power circuit 21 is connected to the control unit 20 by a cable 22 and is connected to the valve 18 by another cable 23.

The conductivity control unit 20 is shown in greater detail in FIGS. 2 and 3. An annular electrode 30 is positioned in one end of an insulating tube 31. Another electrode 32 in the shape of a truncated cone is carried in another insulating tube 33 which is positioned within the tube 31. A circuit board 34 is carried within the tube 33, with the cable 22 connected to the components on the board 34. A metal contact rod 35 has a U bend at one end 36 and is connected to the electrode 30 at this end. The main portion of this rod is positioned along the outer surface of the tube 31.

A bolt 40 is positioned in an opening 41 of the inner tube 33 and passes through a slot 42 in the outer tube 31. The bolt also passes through an opening in a connector member 44 on circuit board 34. An L-shaped bracket 45 is positioned on the exterior of the tube 31 and contacts the rod 35, with the bolt 40 passing through an opening in the bracket 45. The assembly is held together by a wingnut 46 which serves to clamp the inner tube 33, the outer tube 31, the rod 35 and the bracket 45 together.

Although the electrodes 30 and 32 and contact rod 35 are shown as solid metal members, in another preferred embodiment these could be electrical conductors formed by plating or other methods onto nonconducting members of equivalent shape.

The electrodes 30 and 32 form the conductivity cell. The electrode 32 may be moved toward and away from the electrode 30 by loosening the wingnut 46 and sliding the bolt 40 in the slot 42 in the outer tube 31. The electrode 32 may be spaced axially from the electrode 30 various distances, as shown in FIG. 2. Also, the electrode 32 may be positioned within the electrode 30 by moving the electrode 32 to the left as viewed in FIG. 2. In one embodiment now in use, the electrode 32 is movable more than 3 inches with respect to the electrode 30 providing a conductivity setting point variable over more than two decades. When used with normal water, the conductivity setting point is varied over the range of 20 to 3000 micromhos. In an alternative configuration used for deionized water, the conductivity set point is variable over the range of 2 to 300 micromhos. A scale, not shown, reading directly in micromhos may be located parallel to the slot 42 on outer tube 31, with the L bracket 45 serving as a pointer.

Figure 5:
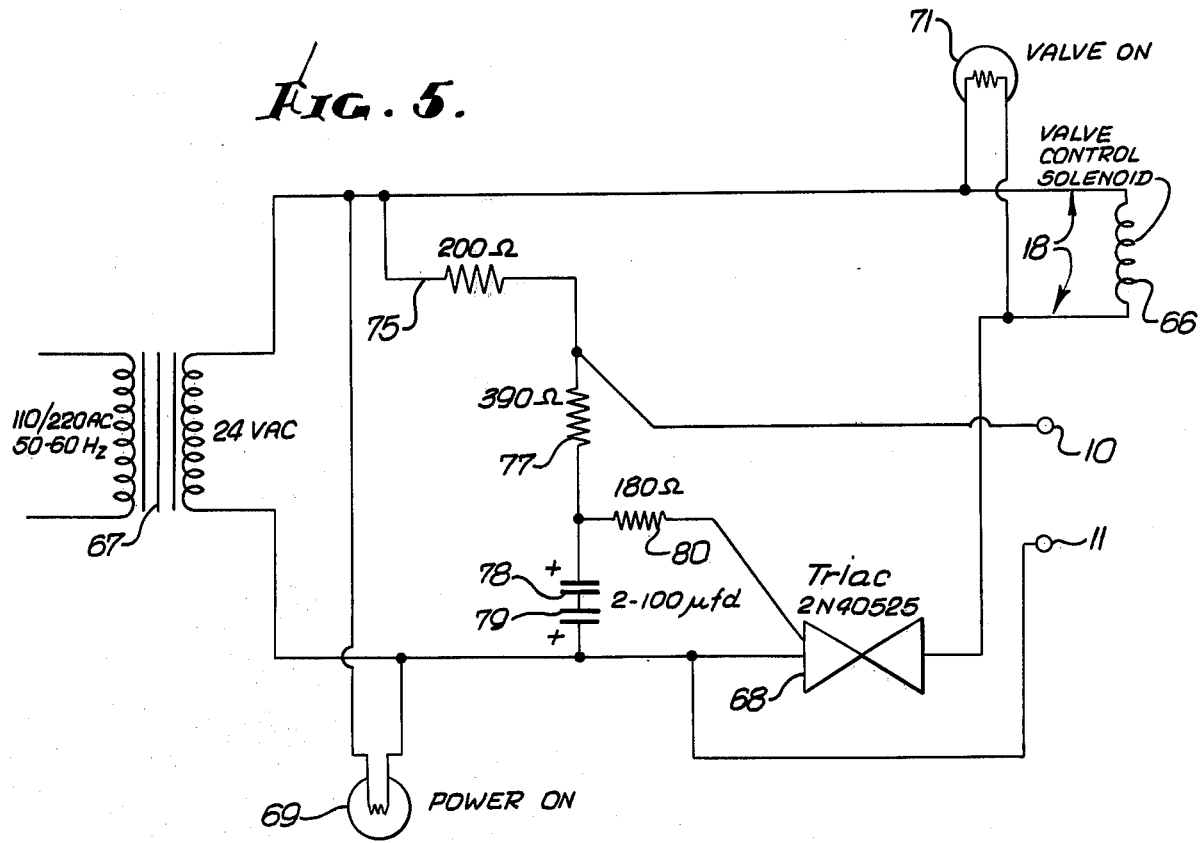
FIG. 5 is a schematic of the power circuit and the valve solenoid.

The presently preferred control circuit for carrying on the circuit board 34 is illustrated in FIG. 4 and the presently preferred arrangement for the power circuit 21 is illustrated in FIG. 5. In the circuit of FIG. 4, a diode 50 is connected across the terminals 10, 11 and a controlled rectifier 51, preferably a silicon controlled rectifier (SCR), is also connected across the terminals with a polarity opposite to that of the diode 50. Resistors 52, 53, 54 are connected in series across the terminals 10, 11, with the electrode 32 connected through a resistor 55 and a capacitor 56 to the junction of the resistors 52, 53. A transistor 60 is connected between the junction of the resistors 52, 53 and the terminal 11, with a zener diode 61 and a capacitor 62 connected in series across the terminals 10, 11 and a resistor 63 connected between the junction of the diode 61 and capacitor 62 and the base of the transistor 60. The terminals 10, 11 of the circuit of FIG. 4 are connected in either polarity to the terminals 10, 11 of the circuit of FIG. 5 by the cable 22.

In the circuit of FIG. 5, a solenoid 66 operates the valve 18 and is connected to the secondary of the transformer 67 by a triac 68 which functions as a power output switch or relay. An indicator lamp 69 is connected across the transformer output to provide an indication of when power is being provided to the unit. Another lamp 71 is connected across the solenoid 66 to provide an indication of when the solenoid is energized. Resistors 75, 77 are connected in series with capacitors 78, 79 across the transformer secondary. The capacitors 78, 79 are connected in opposite polarity so that the circuit is not polarity sensitive. Another resistor 80 is connected between the control electrode of the triac 68 and the junction of the resistor 77 and capacitor 78. Preferred values and types for the components of the circuits of FIGS. 4 and 5 are set out on the drawing. In FIG. 4, resistor 52 has a 5 kohm value for the 2 to 300 micromoh range and 1 kohm for the 20 to 3000 micromoh range.

Under normal operation with the water in satisfactory condition, i.e., the water-contamination conductivity lower than the set point, the tsolenoid 66 is unenergized and the diode 50 and SCR 51 conduct on successive half cycles of the ac power wave. The voltage wave at the terminals 10, 11 has the form shown in FIG. 6. When the water-contamination conductivity increases above the set point, the SCR 51 is not triggered into conduction and the voltage at the terminals 10, 11 has the form of FIG. 7, with the negative half wave being clipped by the diode 50. This half wave rectified voltage at terminals 10, 11 charges one of the capacitors 78, 79 and when charged to a suitable value, the triac 68 is triggered into conduction and energizes the solenoid 66 opening the value 18 and adding water to the tank 15 through the line 17. The system remains in this condition until the SCR 51 again begins to conduct, at which time the triac is no longer triggered and the solenoid 66 is de-energized.

The operation of the circuit of FIG. 4 will be described in greater detail. As the positive half cycle of the voltage at the terminal 10 begins, a corresponding increase in voltage at the control electrode of the SCR 51 occurs. This is the increasing value indicated at 80 in FIG. 6. When the voltage at the control electrode reaches the triggering value, the SCR 51 is fired into conduction for the remainder of the half cycle, with the consequent reduction in voltage as indicated at 81 of FIG. 6. An increase in conductivity of the cell, as measured by the electrodes 30, 32, reduces the impedance in the circuit comprising the capacitor 56, the resistor 55 and the conductivity cell which shunts the control electrode of the SCR. When this occurs, a higher voltage must be reached at the terminal 10 before the SCR will be fired into conduction. As the conductivity at the cell increases, a higher and higher value of voltage at terminal 10 is required to trigger the SCR 51. Finally, the voltage requirement for the condition gets high enough to fire the zener diode 61 into conduction. When the zener diode conducts, the transistor 60 is made conducting, which reduces the voltage across the cell and the voltage to the SCR control electrode. The SCR is not triggered into conduction and the condition illustrated in FIG. 7 results.

This condition continues until the water-contamination conductivity falls by a predetermined amount which is referred to as the latching or hysteresis figure. In the specific circuit illustrated, the cell conductivity has to drop about 5% from the value which opened the water valve before the water valve closes. This figure is controlled by the magnitude of the capacitor 56 and the capacitance of the conductivity cell. When the SCR is conducting, there is positive feedback through the SCR which charges the capacitor 56 and the cell to a potential slightly higher than the potential prior to firing of the SCR. By way of example, in one configuration, the SCR will be fired with a potential of 0.5 volts at point 82. The positive feedback through the SCR will raise point 82 to about 0.6 volts thus charging the capacitors to a slightly higher potential. Then the conductivity of the cell has to drop by about 5% to bring the potential at point 82 below 0.5 so that the SCR does not fire. The latching figure of 5% can be increased to about 8% by omitting the capacitor 56.

By placing the circuitry of FIG. 4 in the inner tube 33 of the conductivity control unit 20, all of the components are maintained at the same temperature as the water and the stability of the control system is improved. The resistor 55 is used for temperature compensation trimming of the circuit. When the SCR 51 gets hotter, it requires a lower voltage for firing. Also when the water gets hotter, the cell conductivity increases. The magnitude of the resistor 55 is chosen to compensate for the difference between these two variables so that this system will maintain precision control of water quality in the rinse tank irrespective of water temperature, up to the boiling point.

The power circuit of FIG. 5 including all connections (terminal strip) are grouped together on one small circuit board positioned on the transformer and all located in a corrosion and splash proof housing. There is no exposed wiring or connections elsewhere. Thus, kept warm and dry, this portion of the system is protected from corrosion and damage even in a severe environment that is wet and filled with corrosive fumes. Also since there are no adjustable controls in this housing, it may be located out of the area of high activity and it always remains closed after installation.

The circuit of FIG. 4 maintains substantially the same waveform across the cell for the solenoid off and solenoid on conditions and therefore permits the cell to always operate under the same conditions. The capacitance effect of the cell surfaces remains substantially the same and the stability of conductivity measurement is enhanced.

The voltage wave across the cell when the SCR is conducting is shown in FIG. 8 and the corresponding wave when the SCR is not conducting is shown in FIG. 9. There is a slight difference in the height of the spikes and there is a small amount of positive voltage following the spike in the SCR conducting, solenoid off condition. For the water off condition, the voltage across the cell increases during the positive half cycle in the same manner that it increases at the terminal 10. Then when the SCR fires, the voltage at terminal 10 is pulled down and there is a corresponding drop in the voltage across the cell. For the solenoid on condition when the SCR does not fire with the resultant positive half wave at the terminal 10 (FIG. 7), the transistor 60 is triggered into conduction and pulls the voltage across the cell down to zero.

While the system is operated at line frequency such as 50 or 60 hertz, the spike waveform at the cell (FIGS. 8 and 9) is equivalent to a high frequency signal and makes the conductivity cell much easier to calibrate and much more stable. Since the spike is controlled by a zener and the cell potential is substantially zero most of the time, the system is insensitive to noise, frequency and voltage changes on the ac power line. All circuit impedances are low and the control circuit is located at the cell to eliminate any pick up of stray electrical interference in the environment. Thus shielded connnecting cables or noise filters are unnecessary. By having large cell volume and electrode areas plus the spiked waveform, environmental factors such as air bubbles, orts, chemicals and scale deposits do not reduce the accuracy of control by the system.

I claim:

1. A conductivity cell for use in a control system for a rinse tank and the like having a tank for water, a water inlet line, flow control means for controlling flow in said inlet line and circuit means for operating said flow control means in response to the conductivity cell, the cell comprising in combination:
   first and second electrodes;
   means for mounting said electrodes in spaced relation for immersion in the tank; and
   means for moving one of said electrodes relative to the other,
   with said first electrode being a sleeve and said second electrode being a plug mounted coaxial with said first electrode for movement along the axis.

2. A cell as defined in claim 1 wherein said first electrode sleeve has an internal taper at one end and said second electrode plug is tapered and movable along the axis between a position spaced from said first electrode and a position within said first electrode.

3. A cell as defined in claim 2 wherin said means for mounting includes:
   a first insulator tube with said first electrode carrier at one end thereof;
   a second insulator tube positioned within said first insulator tube with said second electrode carried at one end thereof and facing said first electrode; and
   means for interconnecting said tubes.

4. A cell as defined in claim 3 wherein said means for moving includes:
   a slot in said first tube;
   a rod connected to said first electrode and disposed on the exterior of said first tube along said slot;
   a stud projecting from said second tube through said slot for movement in said slot; and
   means for clamping said stud, rod and tubes together.

5. A cell as defined in claim 4 including an electronic circuit board positioned within said second tube, with said stud engaging said circuit board positioning said board in said second tube.

6. A conductivity cell for use in a control system for a rinse tank and the like having a tank for water, a water inlet line, flow control means for controlling flow in said inlet line and circuit means for operating said flow control means in response to the conductivity cell, the cell comprising in combination:
   first and second electrodes;
   means for mounting said electrodes in spaced relation for immersion in the tank; and
   means for moving one of said electrodes relative to the other;
   said means for mounting including:
   a first insulator tube with said first electrode carried at one end thereof;
   a second insulator tube positioned within said first insulator tube with said second electrode carried at one end thereof and facing said first electrode; and
   means for interconnecting said tubes.

7. A cell as defined in claim 6 wherein said means for moving includes:
   a slot in said first tube;
   a rod connected to said first electrode and disposed on the exterior of said first tube along said slot;
   a stud projecting from said second tube through said slot for movement in said slot; and
   means for clamping said stud, rod and tubes together.

8. A cell as defined in claim 6 including an electronic circuit board positioned within said second tube for immersion in the tank.

9. A conductivity cell foruse in a control system for a rinse tank and the like having a tank for water, a water inlet line, flow control means for controlling flow in said inlet line and circuit means for operating said flow control means in response to the conductivity cell, the cell comprising in combination:
   first and second electrodes;
   means for mounting said electrodes in spaced relation for immersion in the tank; and
   means for moving one of said electrodes relative to the other;

said circuit means including in combination:
  a pair of terminals;
  means for connecting an ac electrical power source across said terminals;
  a first rectifier connected across said terminals with one polarity;
  a second controlled rectifier connected across said terminals with the opposite polarity;
  a voltage divider connected across said terminals, with a point of said divider connected to the control electrode of said second rectifier for firing said second rectifier;
  first means connecting said cell to said divider circuit in shunt relation with said second rectifier control electrode; and
  second means connected to said divider circuit in shunt relation with said cell for reducing the voltage across said cell when the voltage at said terminals exceeds a predetermined value.

10. A conductivity cell as defined in claim 10 wherein said first means includes a capacitor and resistor connected in series with said cell.

11. A conductivity cell as defined in claim 9 wherein said second means includes:
  a transistor with collector and emitter connected in shunt relation with said cell; and
  a zener diode and a capacitor connected in series across said terminals, with the junction of said zener diode and capacitor connected to the base of said transistor.

12. A conductivity cell as defined in claim 9 wherein said circuit means includes in combination:
  a valve control coil;
  a power switch for connecting said coil to the ac electrical power source, said power switch having a control terminal;
  a first resistor and a first capacitor connected in a series circuit for connection to the ac power source;
  means connecting said power switch control terminal to a point on said first resistor; and
  means connecting said pair of terminals across said first capacitor and at least a portion of said first resistor.

13. A conductivity cell as defined in claim 12 wherein said first means includes a second capacitor and second resistor connected in series with said cell.

14. A conductivity cell as defined in claim 13 wherein said second means includes:
  a transistor with collector and emitter connected in shunt relation with said cell; and
  a zener diode and a third capacitor connected in series across said pair of terminals, with the junction of said zener diode and third capacitor connected to the base of said transistor.

15. A control system for use in a rinse tank and the like having a water inlet line and a valve for controlling flow in said inlet line, including in combination:
  a conductivity cell for positioning in said tank;
  a pair of terminals;
  means for connecting an ac electrical power source across said terminals;
  a first rectifier connected across said terminals with one polarity;
  a second controlled rectifier connected across said terminals with the opposite polarity;
  a voltage divider connected across said terminals, with a point of said divider connected to the control electrode of said second rectifier for firing said second rectifier;
  first means connecting said cell to said divider circuit in shunt relation with said second rectifier control electrode; and
  second means connected to said divider circuit in shunt relation with said cell for reducing the voltage across said cell when the voltage at said terminals exceeds a predetermined value.

16. A conductivity cell as defined in claim 15 wherein said first means includes a capacitor and resistor connected in series with said cell.

17. A conductivity cell as defined in claim 15 wherein said second means includes:
  a transistor with collector and emitter connected in shunt relation with said cell; and
  a zener diode and a capacitor connected in series across said terminals, with the junction of said zener diode and capacitor connected to the base of said transistor.

18. A conductivity cell as defined in claim 15 wherein said circuit means includes in combination:
  a valve control coil;
  a power switch for connecting said coil to the ac electrical power source, said power switch having a control terminal;
  a first resistor and a first capacitor connected in a series circuit for connection to the ac power source;
  means connecting said power switch control terminal to a point on said first resistor; and
  means connecting said pair of terminals across said first capacitor and at least a portion of said first resistor.

19. A conductivity cell as defined in claim 18 wherein said first means includes a second capacitor and second resistor connected in series with said cell.

20. A conductivity cell as defined in claim 19 wherein said second means includes:
  a transistor with collector and emitter connected in shunt relation with said cell; and
  a zener diode and a third capacitor connected in series across said pair of terminals, with the junction of said zener diode and third capacitor connected to the base of said transistor.

* * * * *